United States Patent
Igarashi et al.

(10) Patent No.: US 7,303,826 B2
(45) Date of Patent: Dec. 4, 2007

(54) LIGHT EMITTING ELEMENT AND IRIDIUM COMPLEX

(75) Inventors: Tatsuya Igarashi, Kanagawa (JP); Kohsuke Watanabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 64 days.

(21) Appl. No.: 10/651,230

(22) Filed: Aug. 29, 2003

(65) Prior Publication Data
US 2004/0053071 A1 Mar. 18, 2004

(30) Foreign Application Priority Data
Aug. 29, 2002 (JP) ............... P. 2002-251871

(51) Int. Cl.
H01L 51/54 (2006.01)
(52) U.S. Cl. ............ 428/690; 428/917; 313/504; 313/506; 257/40; 257/102; 257/E51.044
(58) Field of Classification Search ............ None
See application file for complete search history.

(56) References Cited

U.S. PATENT DOCUMENTS

| | | | |
|---|---|---|---|
| 5,281,489 A * | 1/1994 | Mori et al. | 428/690 |
| 5,755,999 A * | 5/1998 | Shi et al. | 252/301.16 |
| 6,458,475 B1 * | 10/2002 | Adachi et al. | 428/690 |
| 6,893,743 B2 * | 5/2005 | Sato et al. | 428/690 |
| 2002/0045065 A1 * | 4/2002 | Kim et al. | 428/690 |
| 2003/0054198 A1 * | 3/2003 | Tsuboyama et al. | 428/690 |
| 2003/0068526 A1 * | 4/2003 | Kamatani et al. | 428/690 |
| 2003/0080342 A1 * | 5/2003 | Igarashi | 257/79 |
| 2004/0001970 A1 * | 1/2004 | Qiu et al. | 428/690 |
| 2005/0244673 A1 * | 11/2005 | Satoh et al. | 428/690 |

FOREIGN PATENT DOCUMENTS

| | | |
|---|---|---|
| WO | WO 01/41512 A1 | 6/2001 |
| WO | WO 02/44189 A1 | 6/2002 |
| WO | WO 02/45466 A1 | 6/2002 |
| WO | WO 02/064700 A1 | 8/2002 |
| WO | WO 03/001616 A2 | 1/2003 |

OTHER PUBLICATIONS

Baldo et al., "Vey high-efficiency green organic light-emitting devices based on electrophosphorescence", Applied Physics Letters, vol. 75, No. 1—Jul. 5, 1999, pp. 4-6.
Yuichiro Kawamura et al., "Energy transfer in polymer electrophosphorescent light emitting devices with single and multiple doped luminescent layers", J. App. Physics., vol. 92, No. 1 pp. 87-93, Jul. 1, 2002.
European Search Report dated Jan. 14, 2004.

* cited by examiner

*Primary Examiner*—Marie Yamnitzky
(74) *Attorney, Agent, or Firm*—Sughrue Mion Pllc.

(57) ABSTRACT

An organic electroluminescent element comprising: a pair of electrodes; and at least one organic layer provided between the pair of electrodes, at least one of the at least one organic layer being a light emitting layer, wherein the light emitting layer comprises at least one transition metal complex represented by the formula (1), (2), (3), (4) or (5) as defined herein or an iridium complex represented by the formula (A), (6), (7) or (8) as defined herein.

2 Claims, No Drawings

LIGHT EMITTING ELEMENT AND IRIDIUM COMPLEX

FIELD OF THE INVENTION

The present invention relates a light emitting element capable of converting an electric energy into a light to cause light emission. Also, the invention relates to a novel iridium complex that can suitably be used in the light emitting element. Especially, the light emitting element of the invention can suitably be utilized in organic electroluminescent (EL) elements.

BACKGROUND OF THE INVENTION

At present, research and development of various display elements are active. Especially, organic electroluminescent (EL) elements can obtain light emission with a high luminance at a low voltage, and therefore, are noticed as a promising display element.

As measures for enhancing characteristics of light emitting elements, there is reported a green light emitting element utilizing light emission from an ortho-metalated iridium complex (Ir(ppy)$_3$:Tris-Ortho-Metalated Complex of Iridium(III) with 2-Phenylpyridine) (see *Applied Physics Letters*, 75, 4 (1999)). This element attains an external quantum yield of 8%, which is superior to an external quantum yield of 5% that has hitherto been considered to be a limit in conventional elements. However, since this element is still low in efficiency and is limited to green light emission, it is narrow with respect to the range of application as a display. Thus, development of light emitting elements of other colors with a high efficiency has been demanded.

Complexes having a picolinic acid ligand and light emitting elements containing the same are disclosed (for example, see WO 01/41512, WO 02/44189 and WO 02/45466). However, light emitting elements containing a complex that can be driven at a lower voltage and can undergo light emission with a high luminance are demanded.

SUMMARY OF THE INVENTION

An object of the invention is to provide a light emitting element that can undergo light emission with a high luminance in a high efficiency and emits a light to multiple colors (especially brown to red colors).

Another object of the invention is to provide a transition metal complex that is used in the multicolor light emitting element.

The foregoing objects of the invention are attained by light emitting elements having the following constructions and transition metal complexes.

1. A light emitting element comprising at least one light emitting layer-containing organic layer between a pair of electrodes, the light emitting layer containing at least one transition metal complex represented by the following formula (1).

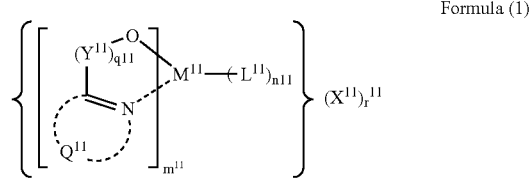

Formula (1)

In the formula (1), $Q^{11}$ represents a group of forming a nitrogen-containing condensed aromatic ring; $Y^{11}$ represents a connecting group (linking group); $M^{11}$ represents a transition metal ion; $L^{11}$ represents a ligand; $X^{11}$ represents a counter ion; $Y^{11}$ cannot be bonded to $Q^{11}$ to form an 8-hydroxyquinolinol ligand; $n^{11}$ represents an integer of from 0 to 4; $m^{11}$ represents an integer of from 1 to 4; $q^{11}$ represents an integer of from 0 to 3; and $r^{11}$ represents an integer of from 0 to 3.

2. The light emitting element according to the foregoing item 1, wherein the transition metal complex represented by the formula (1) is a transition metal complex represented by the following formula (2).

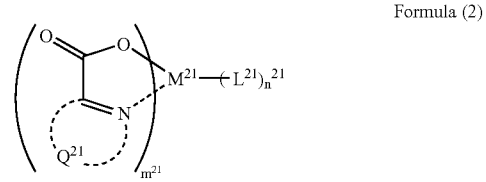

Formula (2)

In the formula (2), $Q^{21}$ represents a group of forming a nitrogen-containing condensed aromatic ring; $M^{21}$ represents a transition metal ion; $L^{21}$ represents a ligand; $n^{21}$ represents an integer of from 0 to 4; and $m^{21}$ represents an integer of from 1 to 4.

3. The light emitting element according to the foregoing item 2, wherein the transition metal complex represented by the formula (2) is an iridium complex represented by the following formula (3).

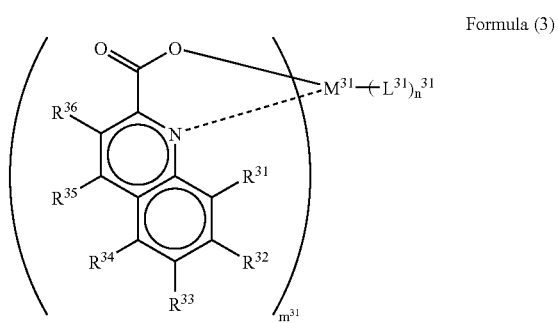

Formula (3)

In the formula (3), $R^{31}$, $R^{32}$, $R^{33}$, $R^{34}$, $R^{35}$, and $R^{36}$ each independently represents a hydrogen atom or a substituent, and adjacent groups thereof may be bonded to each other to form a condensed ring structure; $L^{31}$ represents a ligand; $n^{31}$ represents an integer of from 0 to 4; and $m^{31}$ represents an integer of from 1 to 3.

4. The light emitting element according to the foregoing item 2, wherein the transition metal complex represented by the formula (2) is an iridium complex represented by the following formula (4).

Formula (4)

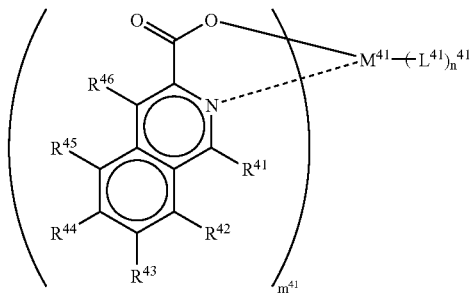

In the formula (4), $R^{41}$ $R^{42}$, $R^{43}$ $R^{44}$ $R^{45}$, and $R^{46}$ each independently represents a hydrogen atom or a substituent, and adjacent groups thereof may be bonded to each other to form a condensed ring structure; $L^{41}$ represents a ligand; $m^{41}$ represents an integer of from 1 to 3; and $n^{41}$ represents an integer of from 0 to 4.

5. The light emitting element according to the foregoing item 2, wherein the transition metal complex represented by the formula (2) is an iridium complex represented by the following formula (5).

Formula (5)

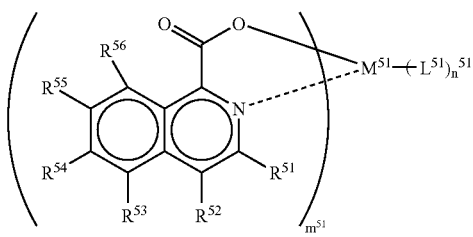

In the formula (5), $R^{51}$, $R^{52}$, $R^{53}$, $R^{54}$, $R^{55}$, and $R^{56}$ each independently represents a hydrogen atom or a substituent, and adjacent groups thereof may be bonded to each other to form a condensed ring structure; $L^{51}$ represents a ligand; $m^{51}$ represents an integer of from 1 to 3; and $n^{51}$ represents an integer of from 0 to 4.

6. An iridium complex represented by the following formula (A).

Formula (A)

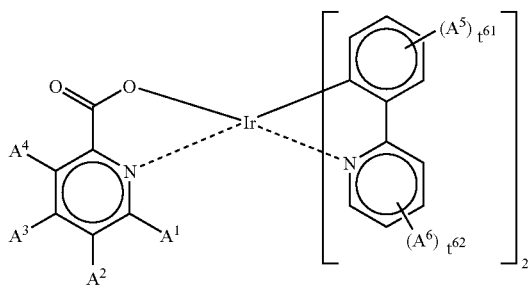

In the formula (A), wherein $A^1$, $A^2$, $A^3$, and $A^4$ each independently represents a hydrogen atom or a substituent, and adjacent groups thereof may be bonded to each other to form a benzene ring; $A^5$ and $A^6$ each independently represents a substituent; and $t^{61}$ and $t^{62}$ each independently represents an integer of from 0 to 4.

7. An iridium complex represented by the following formula (6).

Formula (6)

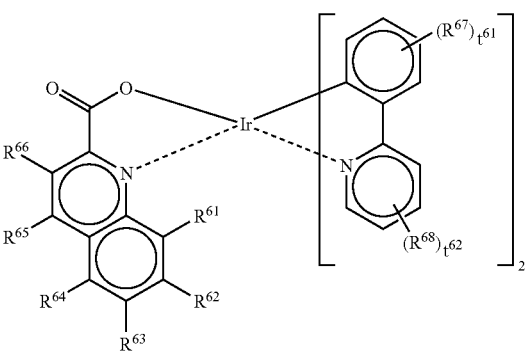

In the formula (6), $R^{61}$, $R^{62}$, $R^{63}$ $R^{64}$, $R^{65}$, and $R^{66}$ each independently represents a hydrogen atom or a substituent; $R^{67}$ and $R^{68}$ each independently represents a substituent; and $t^{61}$ and $t^{62}$ each independently represents an integer of from 0 to 4.

8. An iridium complex represented by the following formula (7).

Formula (7)

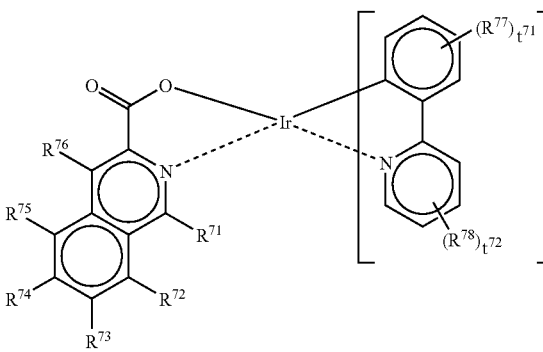

In the formula (7), $R^{71}$, $R^{72}$, $R^{73}$, $R^{74}$, $R^{75}$, and $R^{76}$ each independently represents a hydrogen atom or a substituent; $R^{77}$ and $R^{78}$ each independently represents a substituent; and $t^{71}$ and $t^{72}$ each independently represents an integer of from 0 to 4.

9. An iridium complex represented by the following formula (8).

Formula (8)

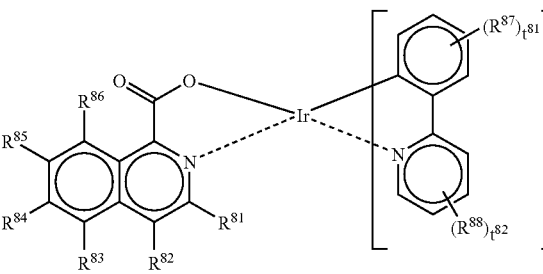

In the formula (8), $R^{81}$, $R^{82}$, $R^{83}$, $R^{84}$, $R^{85}$, and $R^{86}$ each independently represents a hydrogen atom or a substituent; $R^{87}$ and $R^{88}$ each independently represents a substituent; and $t^{81}$ and $t^{82}$ each independently represents an integer of from 0 to 4.

10. The organic electroluminescent element according to the foregoing item 1, wherein at least one of $Y^{11}$s' is an arylene connecting group, a hetero-arylene connecting group, an alkylene connecting group, or an alkenylene group.

11. The organic electroluminescent element according to the foregoing item 1, having a bond between $Y^{11}$ and $Q^{11}$ to form a condensed ring structure.

12. The organic electroluminescent element according to any one of the foregoing items 1, 2, 10 and 11, wherein $Q^{11}$ and $Q^{21}$ each represents a nitrogen-containing condensed aromatic ring group having three or more rings.

13. The organic electroluminescent element according to any one of the foregoing items 1, 2, 10, 11 and 12, wherein $n^{11}$ is 0.

14. The organic electroluminescent element according to any one of the foregoing items 1 to 5 and 10 to 13, wherein the bonds between $M-L^{11}$, $M-L^{21}$, $M-L^{31}$, $M-L^{41}$ and $M-L^{51}$ are each constituted of only nitrogen-metal bond, oxygen-metal coordinate bond, or sulfur-metal coordinate bond.

15. The organic electroluminescent element according to any one of the foregoing items 1 to 14, wherein the light emitting layer contains at least two kinds of host materials and at least one kind of the compound represented by the general formula (1).

16. The organic electroluminescent element according to the foregoing item 15, containing at least one hole transporting host material and at least one electron transporting host material.

17. The organic electroluminescent element according to the foregoing item 16, wherein the hole transporting host material is an amine derivative.

18. The organic electroluminescent element according to the foregoing item 17, wherein the electron transporting host material is a metal complex.

DETAILED DESCRIPTION OF THE INVENTION

The formula (I) will be described below.

$Q^{11}$ represents a group of forming a nitrogen-containing condensed aromatic ring. The number of nitrogen atoms contained in the nitrogen-containing condensed aromatic ring is preferably from 1 to 3, more preferably 1 or 2, and further preferably 1. The nitrogen-containing condensed aromatic ring may contain an oxygen atom and a sulfur atom other than a nitrogen atom or atoms and carbon atoms.

The number of condensed rings of the nitrogen-containing condensed aromatic ring is not particularly limited but is preferably from 2 to 5, more preferably from 2 to 4, further preferably from 2 to 3, and particularly preferably 2.

As nitrogen-containing aromatic rings of forming a nitrogen-containing condensed aromatic ring are preferable 5-membered rings (such as pyrrole, pyrazole, imidazole, thiazole, and oxazole) and 6-membered rings (such as pyridine, pyrazine, and pyrimidine), with 6-membered rings being more preferred.

Examples of nitrogen-containing condensed aromatic rings include condensed ring bodies of pyrrole, pyrazole, imidazole, thiazole, oxazole, pyridine, pyrazine, and pyrimidine (such as condensed ring bodies with benzene, naphthalene, anthracene, pyrene, perylene, triphenylene, pyridine, pyrazine, pyrimidine, quinoline, quinoxaline, thiophene, furan, etc.). As the nitrogen-containing condensed aromatic ring are preferable quinoline, isoquinoline, quinoxaline, and benzoazoles (such as benzoimidazole, benzoxazole, and benzothiazole), more preferable quinoline and isoquinoline, and futher preferable isoquinoline.

$Q^{11}$ may have a substituent. Examples of substituents on $Q^{11}$ include alkyl groups (preferably ones having from 1 to 30 carbon atoms, more preferably ones having from 1 to 20 carbon atoms, and particularly preferably ones having from 1 to 10 carbon atoms, such as methyl, ethyl, isopropyl, tert-butyl, n-octyl, n-decyl, n-hexadecyl, cyclopropyl, cyclopentyl, and cyclohexyl), alkenyl groups (preferably ones having from 2 to 30 carbon atoms, more preferably ones having from 2 to 20 carbon atoms, and particularly preferably ones having from 2 to 10 carbon atoms, such as vinyl, allyl, 2-butenyl, and 3-pentenyl), alkynyl groups (preferably ones having from 2 to 30 carbon atoms, more preferably ones having from 2 to 20 carbon atoms, and particularly preferably ones having from 2 to 10 carbon atoms, such as propargyl and 3-pentynyl), aryl groups (preferably ones having from 6 to 30 carbon atoms, more preferably ones having from 6 to 20 carbon atoms, and particularly preferably ones from 6 to 12 carbon atoms, such as phenyl, p-methylphenyl, naphthyl, and anthranyl), amino groups (preferably ones having from 0 to 30 carbon atoms, more preferably ones having from 0 to 20 carbon atoms, and particularly preferably ones having from 0 to 10 carbon atoms, such as amino, methylamino, dimethylamino, diethylamino, dibenzylamino, diphenylamino, and ditolylamino), alkoxy groups (preferably ones having from 1 to 30 carbon atoms, more preferably ones having from 1 to 20 carbon atoms, and particularly preferably ones having from 1 to 10 carbon atoms, such as methoxy, ethoxy, butoxy, and 2-ethylhexyloxy), aryloxy groups (preferably ones having from 6 to 30 carbon atoms, more preferably ones having from 6 to 20 carbon atoms, and particularly preferably ones having from 6 to 12 carbon atoms, such as phenyloxy, 1-naphthyloxy, and 2-naphthyloxy), heterocyclic oxy groups (preferably ones having from 1 to 30 carbon atoms, more preferably ones having from 1 to 20 carbon atoms, and particularly preferably ones having from 1 to 12 carbon atoms, such as pyridyloxy, pyrazyloxy, pyrimidyloxy, and quinolyloxy), acyl groups (preferably ones having from 1 to 30 carbon atoms, more preferably ones having from 1 to 20 carbon atoms, and particularly preferably ones having from 1 to 12 carbon atoms, such as acetyl, benzoyl, formyl, and pivaroyl), alkxoycarbonyl groups (preferably ones having from 2 to 30 carbon atoms, more preferably ones having from 2 to 20 carbon atoms, and particularly preferably ones having 2 to 12 carbon atoms, such as methoxycarbonyl and ethoxycarbonyl), aryloxycarbonyl groups (preferably ones having from 7 to 30 carbon atoms, more preferably ones having from 7 to 20 carbon atoms, and particularly preferably ones having from 7 to 12 carbon atoms, such as phenyloxycarbonyl), sulfonyl groups (preferably ones having from 1 to 30 carbon atoms, more preferably ones having from 1 to 20 carbon atoms, and particularly preferably ones having from 1 to 12 carbon atoms, such as mesyl and tosyl), a hydroxyl group, heterocyclic groups (preferably ones having from 1 to 30 carbon atoms, and more preferably ones having from 1 to 12 carbon atoms; examples of hetero atoms include a nitrogen atom, an oxygen atom, and a sulfur atom; and specific examples of heterocyclic groups include imidazolyl, pyridyl, quinolyl, furyl, thienyl, piperidyl, morpholino, benzoxazolyl, benzimidazolyl, benzthiazolyl, carbazolyl, and azevinyl), silyl groups (preferably ones having from 3 to 40 carbon atoms, more preferably ones having from 3 to 30 carbon atoms, and particularly preferably ones having from 3 to 24 carbon atoms, such as trimethylsilyl and triphenylsilyl), and silyloxy groups (preferably ones having from 3 to 40 carbon atoms, more preferably ones having from 3 to 30 carbon atoms, and particularly preferably ones having from 3 to 24 carbon atoms, such as trimethylsilyloxy and triphenylsilyloxy). These substituents may further be substituted.

$Y^{11}$ represents a connecting group. The connecting group is not particularly limited but is preferably an alkylene group, an arylene group, a carbonylene group, an —O— group, or an —NR$^a$— group (R$^a$ represents a hydrogen atom or a substituent, and examples of substituents include an alkyl group, an aryl group, and a heterocyclic group), more preferably an alkylene group, a carbonylene group, or an —O— group, and further preferably a carbonylene group. $Y^{11}$ cannot be bonded to $Q^{11}$ to form an 8-hydroxyquinolinol ligand.

$M^{11}$ represents a transition metal ion. The transition metal ion is not particularly limited but is preferably an iridium ion, a platinum ion, a rhenium ion, or a ruthenium ion, more preferably an iridium ion or a platinum ion, and particularly preferably an iridium ion.

$L^{11}$ represents a ligand. Examples of ligands include ligands described in H. Yersin, *Photochemistry and Photophysics of Coordination Compounds*, published by Springer-Verlag (1987) and Akio Yamamoto, *Organometallic Chemistry—Principles and Applications—*, published by Shokabo Publishing Co., Ltd. (1982); preferably halogen ligands (preferably a chlorine ligand and a fluorine ligand), nitrogen-containing heterocyclic ligands (such as bipyridyl, phenanthroline, phenylpyridine, pyrazoylpyridine, and benzimidazolylpyridine), a diketo ligand, a nitrile ligand, a CO ligand, an isonitrile ligand, phosphorus ligands (such as phosphine derivatives, phosphorous acid ester derivatives, and phosphinine derivatives), and carboxylic acid ligands (such as an acetic acid ligand); and more preferably bidentate nitrogen-containing heterocyclic ligands (such as bipyridyl, phenanthroline, phenylpyridine, pyrazoylpyridine, and benzimidazolylpyridine).

$X^{11}$ represents a counter ion. The counter ion is not particularly limited but is preferably an alkali metal ion, an alkaline earth metal ion, a halogen ion, a perchlorate ion, a $PF_6$ ion, an ammonium ion (such as a tetramethylammonium ion), a borate ion, or a phosphonium ion, and more preferably a perchlorate ion or a $PF_6$ ion.

$n^{11}$ represents an integer of from 0 to 4, preferably from 0 to 3, and more preferably from 0 to 2.

$m^{11}$ represents an integer of from 1 to 4, and preferably from 1 to 3.

$q^{11}$ represents an integer of from 0 to 3, preferably 1 or 2, and more preferably 1.

$r^{11}$ represents an integer of from 0 to 3, preferably from 0 to 2, more preferably 0 or 1, and further preferably 0.

The transition metal complex represented by the formula (1) is preferably a transition metal complex represented by the formula (2); more preferably an iridium complex represented by the formula (3), the formula (4), or the formula (5) (above all, the iridium complex represented by the formula (3) or the formula (4) is preferable, and the iridium complex represented by the formula (4) is more preferable); and further preferably an iridium complex represented by the formula (6), the formula (7), or the formula (8) (above all, the iridium complex represented by the formula (6) or the formula (7) is preferable, and the iridium complex represented by the formula (6) is more preferable).

In the compound represented by the general formula (1), it is preferable that at least one of $Y^{11}$s' represents an arylene connecting group (such as a phenylene connecting group, a naphthalene connecting group, a phenanthrene connecting group, and a triphenylene connecting group), a hetero-arylene connecting group (such as a pyridine connecting group, a pyrazine connecting group, a pyrimidine connecting group, a pyridazine group, a pyrrole group, a pyrazole group, and an imidazole group), an alkylene connecting group (such as a methylene connecting group and an ethylene connecting group), or an alkenylene connecting group (such as a vinylene connecting group); it is more preferable that at least one of $Y^{11}$s' represents an arylene connecting group or a hetero-arylene connecting group; and it is further preferable that $Y^{11}$ represents an arylene connecting group. When $Y^{11}$ represents an arylene connecting group, examples of ligands include an o-hydroxyphenyl quinoline ligand and an o-hydroxyphenyl isoquinoline ligand.

In the compound represented by the general formula (1) it is also preferable that a bond is contained between $Y^{11}$ and $Q^{11}$ to form a condensed ring structure (such as a benzo condensed ring, a pyrizo condensed ring, and a pyrrolo condensed ring) (for example, an 8-quinolinecarboxylic acid ligand).

In the compound represented by the general formula (1) or (2), each $Q^{11}$ and $Q^{21}$ preferably represents a nitrogen-containing condensed aromatic ring group having three or more rings, more preferably a nitrogen-containing condensed aromatic ring group having three or four rings, further preferably an azaphenanthrene ring or an azatriphenylene ring, and especially preferably an azaphenanthrene ring.

In the compound represented by the general formula (1) or (2), it is more preferable that $n^{11}$ is 0.

In the compounds represented by the general formulae (1) to (5), the bonds between M-$L^{11}$, M-L 21, M-L 31, M-$L^{41}$ and M-$L^{51}$ are each preferably constituted of only nitrogen-metal bond, oxygen-metal coordinate bond, or sulfur-metal coordinate bond, and more preferably constituted of only nitrogen-metal bond or oxygen-metal coordinate bond.

The formula (2) will be described below. $Q^{21}$, $M^{21}$, and $L^{21}$ are synonymous with the foregoing $Q^{11}$, $M^{11}$ and $L^{11}$, examples of which are also the same. $n^{21}$ represents an integer of from 0 to 4, preferably from 0 to 3, and more preferably from 0 to 2. $m^{21}$ represents an integer of from 1 to 4, and preferably from 1 to 3.

The formula (3), the formula (4), and the formula (5) will be described below. $R^{31}$, $R^{32}$, $R^{33}$, $R^{34}$, $R^{35}$, $R^{36}$, $R^{41}$, $R^{42}$, $R^{43}$, $R^{44}$, $R^{45}$, $R^{46}$, $R^{51}$, $R^{52}$, $R^{53}$, $R^{54}$, $R^{55}$, and $R^{56}$ each independently represents a hydrogen atom or a substituent, and adjacent groups thereof may be bonded to each other to form a condensed ring structure. As the substituent, are enumerated the groups described above for the substituent on $Q^{11}$. $R^{31}$, $R^{32}$, $R^{33}$, $R^{34}$, $R^{35}$, $R^{36}$, $R^{41}$, $R^{42}$, $R^{43}$, $R^{44}$, $R^{45}$, $R^{46}$, $R^{51}$, $R^{52}$, $R^{53}$, $R^{54}$, $R^{55}$, and $R^{56}$ each preferably represents a hydrogen atom, an alkyl group, an aryl group, or a group to form a condensed structure (such as a benzo condensed ring) together with an adjacent group thereof, and more preferably a hydrogen atom or an alkyl group.

$M^{31}$, $M^{41}$, and $M^{51}$ are synonymous with the foregoing $M^{21}$, examples of which are also the same.

$L^{31}$, $L^{41}$, and $L^{51}$ are synonymous with the foregoing $L^{11}$, examples of which are also the same.

$m^{31}$, $m^{41}$, and $m^{51}$ each represents an integer of from 1 to 3, preferably 1 or 2, and more preferably 1. $n^{31}$, $n^{41}$, and $n^{51}$ each represents an integer of from 0 to 4, preferably 1 or 2, and more preferably 2.

The formula (6), the formula (7), and the formula (8) will be described below.

$R^{61}$, $R^{62}$, $R^{63}$, $R^{64}$, $R^{65}$, $R^{66}$, $R^{71}$, $R^{72}$, $R^{73}$, $R^{74}$, $R^{75}$, $R^{76}$, $R^{81}$, $R^{82}$, $R^{83}$, $R^{84}$, $R^{85}$, and $R^{86}$ are synonymous with the foregoing $R^{31}$, $R^{32}$, $R^{33}$, $R^{34}$, $R^{35}$, $R^{36}$, $R^{41}$, $R^{42}$, $R^{43}$, $R^{44}$, $R^{45}$, $R^{46}$, $R^{51}$, $R^{52}$, $R^{53}$, $R^{54}$, $R^{55}$, and $R^{56}$, respectively, examples of which are also the same.

$R^{67}$, $R^{68}$, $R^{77}$, $R^{78}$, $R^{87}$, and $R^{88}$ each independently represents a substituent. As the substituent, are enumerated the groups described above for the substituent on $Q^{11}$. $R^{67}$, $R^{68}$, $R^{77}$, $R^{78}$, $R^{87}$, and $R^{88}$ are each preferably an alkyl group, an aryl group, an alkoxy group, or a halogen atom (preferably a fluorine atom), and more preferably an alkyl group or a fluorine atom.

$t^{61}$, $t^{62}$, $t^{71}$, $t^{72}$, $t^{81}$, and $t^{82}$ each independently represents an integer of from 0 to 4, preferably from 0 to 2, more preferably 0 or 1, and further preferably 0.

The transition metal complex of the invention may be a low-molecular weight compound or may be an oligomer compound or a polymer compound (the weight average molecular weight (as reduced into polystyrene) is preferably from 1,000 to 500,000, more preferably from 2,000 to 100,000, and more preferably from 3,000 to 100,000). In the case of polymer compounds, the structure represented by the formula (1) may be contained in the polymer main chain or may be contained in the polymer side chains. Further, in the case of polymer compounds, they may be a homopolymer compound or a copolymer. The compound of the invention is preferably a low-molecular weight compound.

In the invention, the transition metal complex represented by the formula (1) is preferably contained in an amount of from 1% by weight to 20% by weight, more preferably from 1% by weight to 10% by weight, and further preferably from 3% by weight to 8% by weight in the light emitting layer.

Compound examples of the transition metal complex of the invention will be given below, but it should not be construed that the invention is limited thereto.

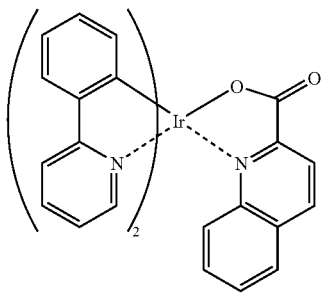

(1-1)

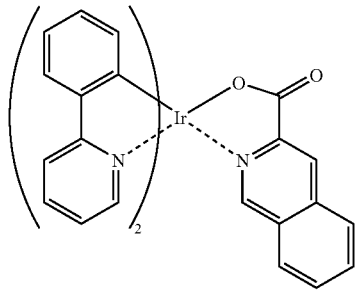

(1-2)

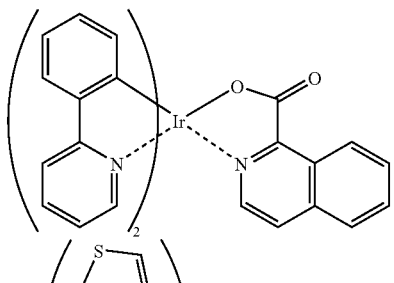

(1-3)

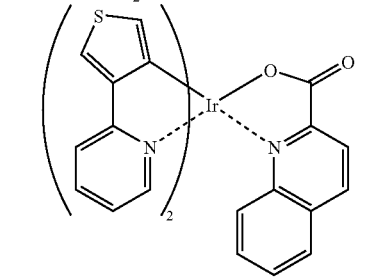

(1-4)

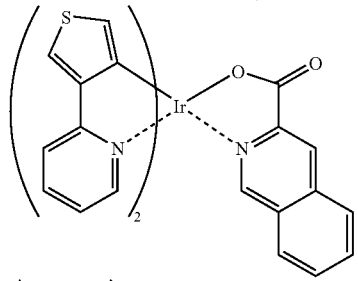

(1-5)

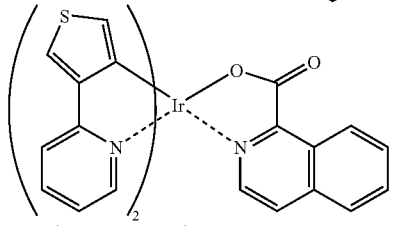

(1-6)

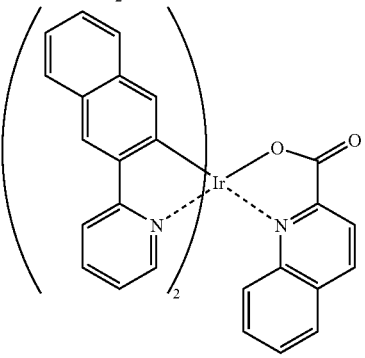

(1-7)

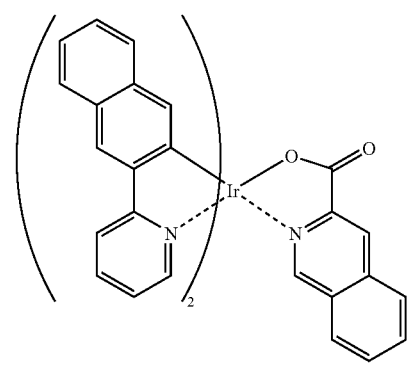
(1-8)
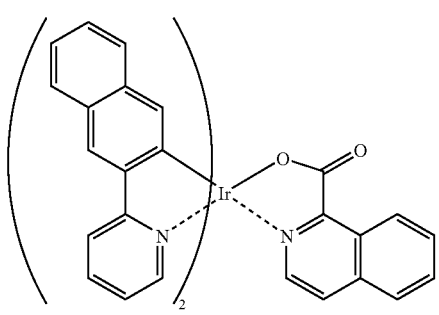
(1-9)
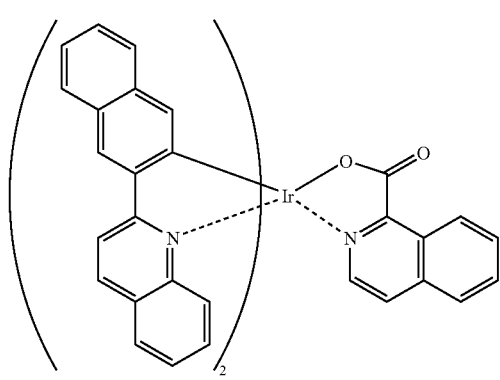
(1-10)
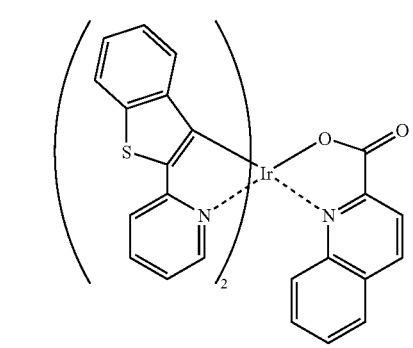
(1-11)
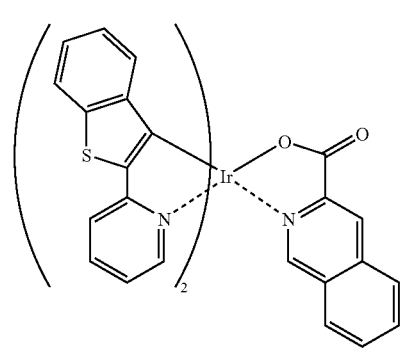
(1-12)
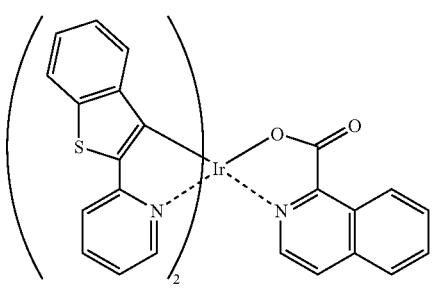
(1-13)
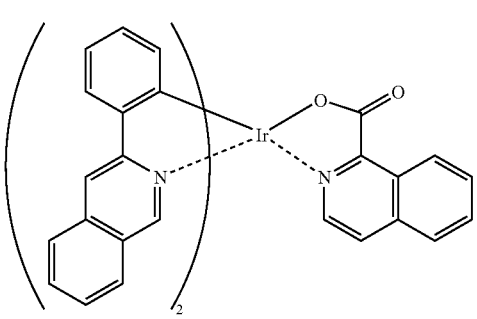
(1-14)
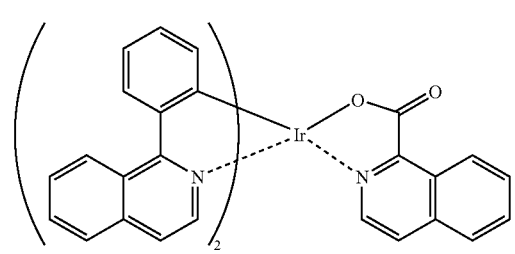
(1-15)
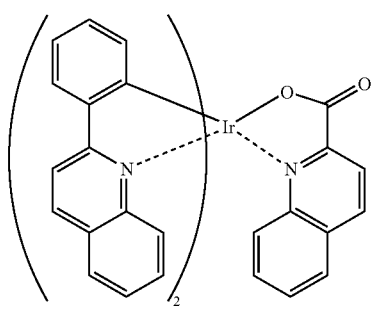
(1-16)

-continued
(1-17)
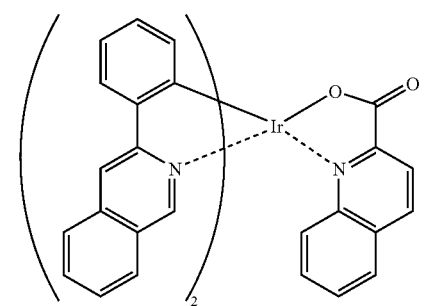
(1-18)
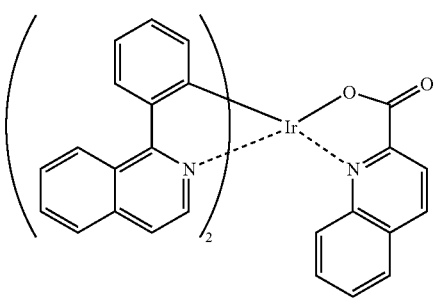
(1-19)
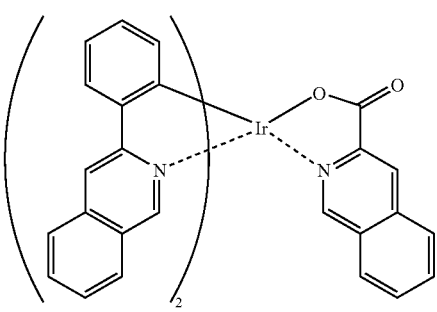
(1-20)
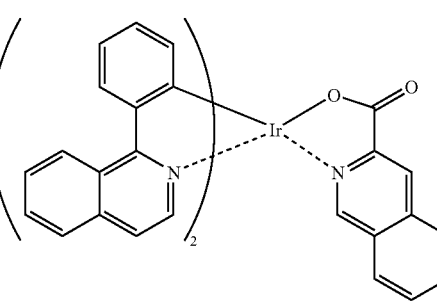
(1-21)
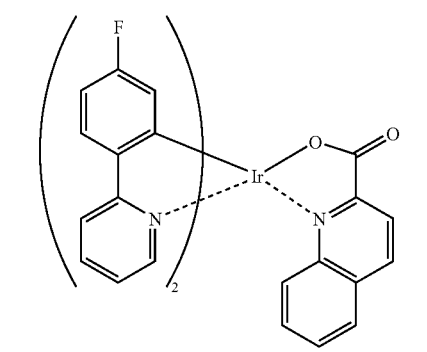
-continued
(1-22)
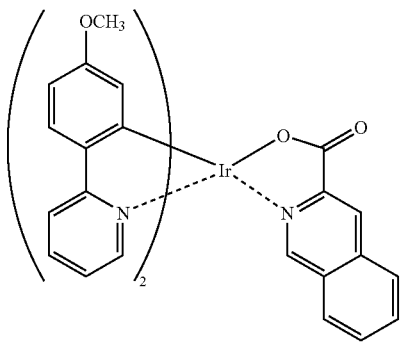
(1-23)
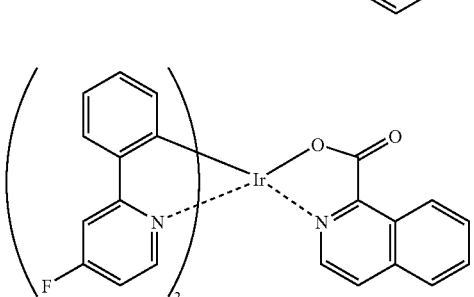
(1-24)
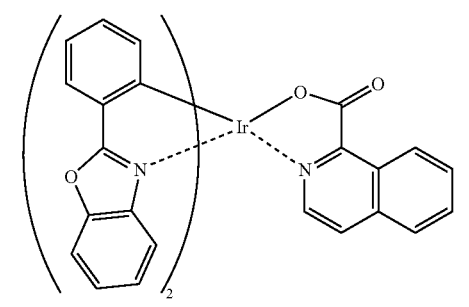
(1-25)
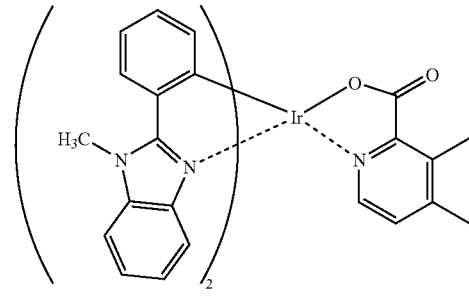
(1-26)
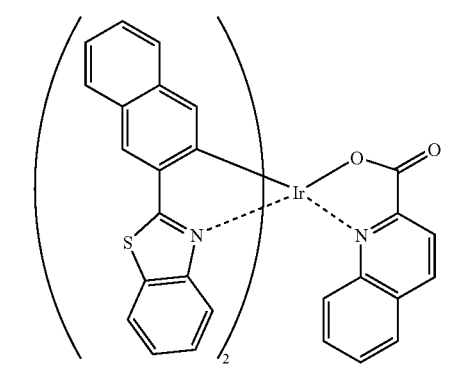

-continued
(1-27)
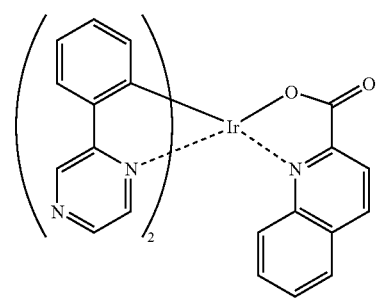
(1-28)
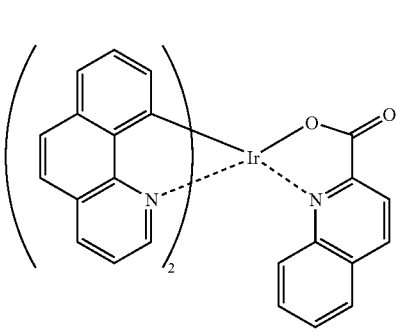
(1-29)
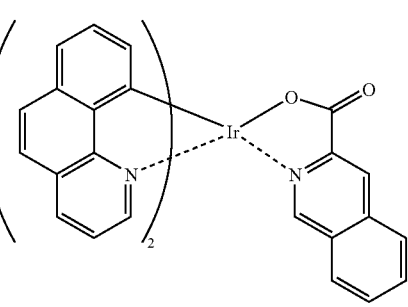
(1-30)
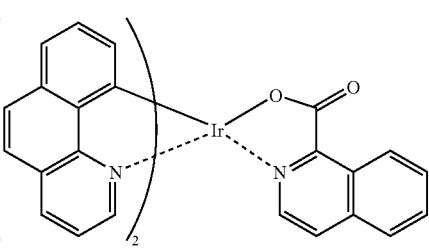
(1-31)
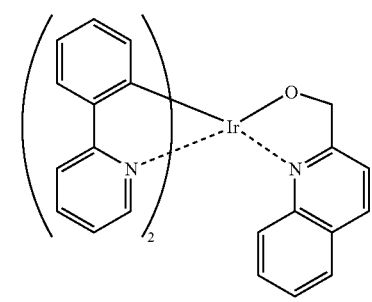
-continued
(1-32)
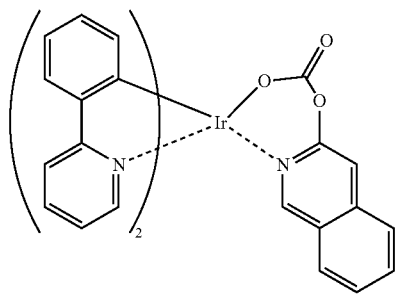
(1-33)
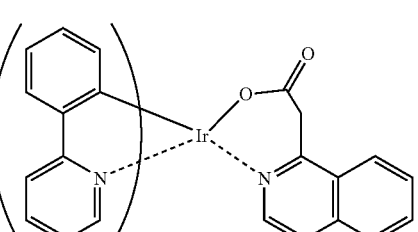
(1-34)
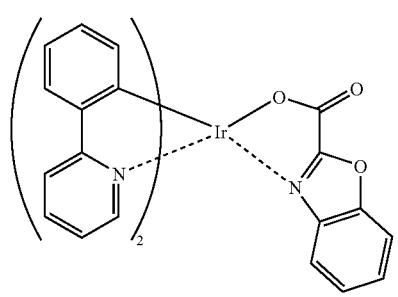
(1-35)
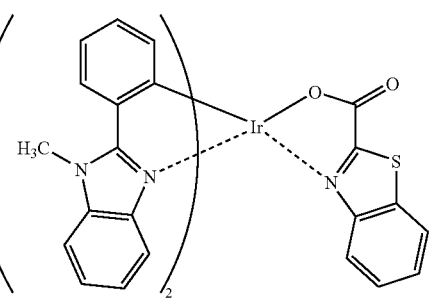
(1-36)
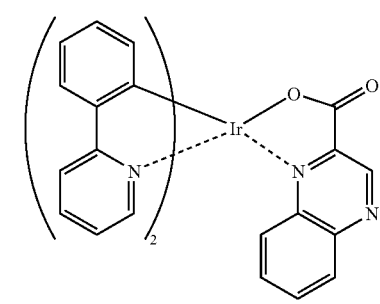

(1-37)
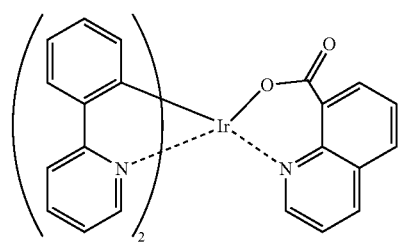
(1-38)
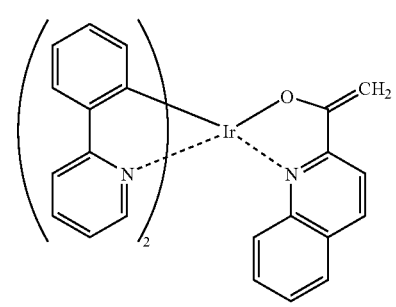
(1-39)
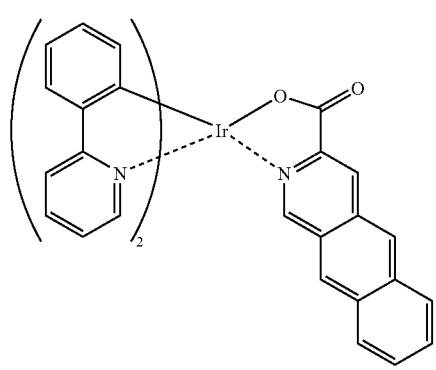
(1-40)
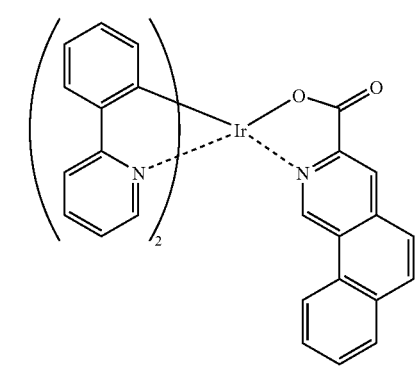
(1-41)
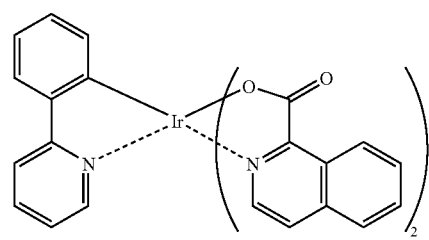
(1-42)
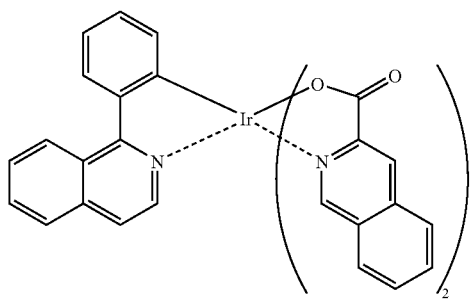
(1-43)
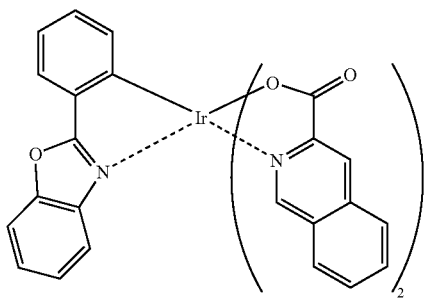
(1-44)
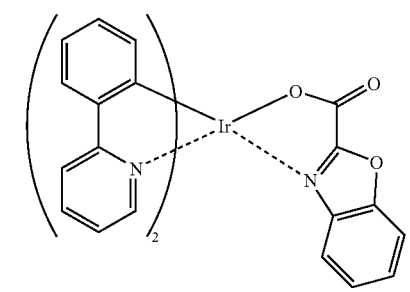
(1-45)
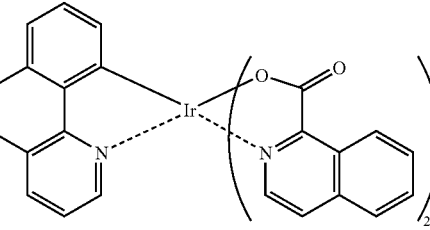
(1-46)
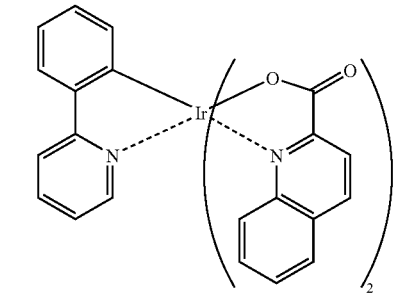

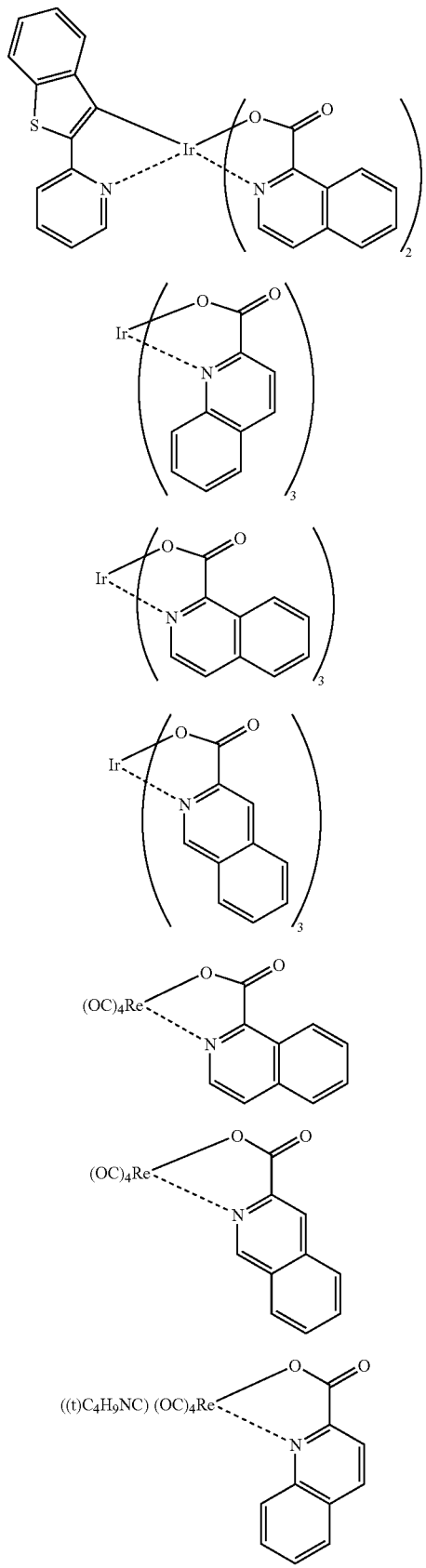
(1-47)
(1-48)
(1-49)
(1-50)
(1-51)
(1-52)
(1-53)
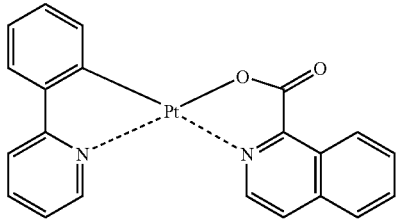
(1-54)
(1-55)
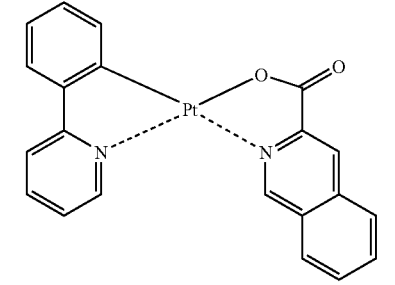
(1-56)
(1-57)
(1-58)
(1-59)

-continued
(I-60)
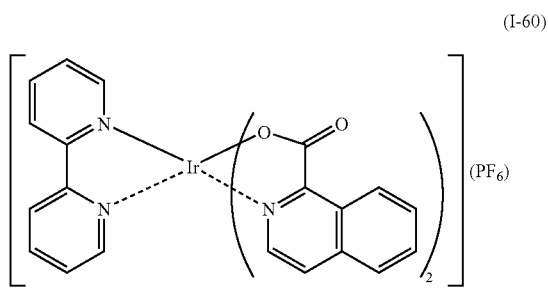
(I-61)
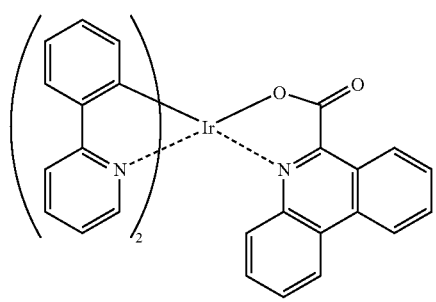
(I-62)
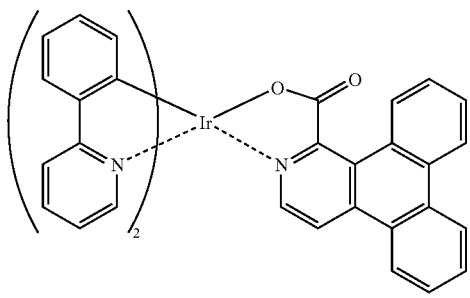
(1-63)
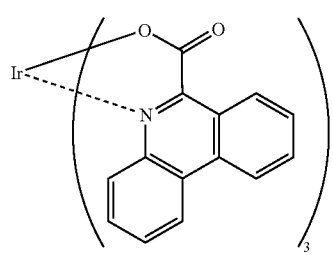
(1-64)
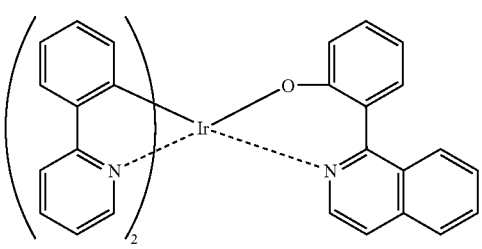
-continued
(1-65)
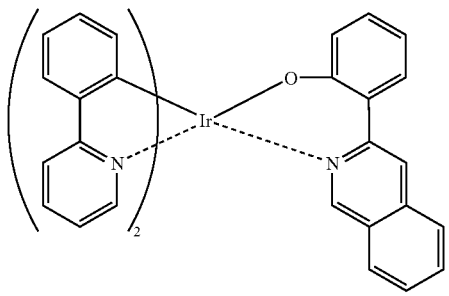
(1-66)
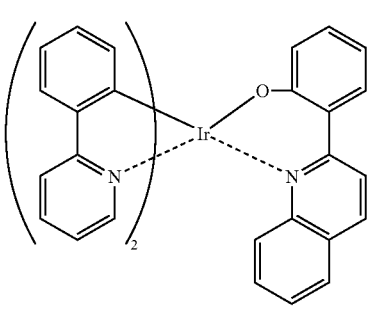
(1-67)
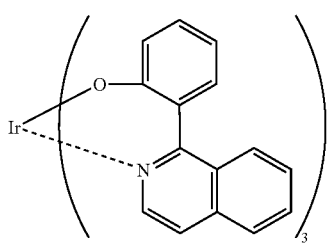
(1-68)
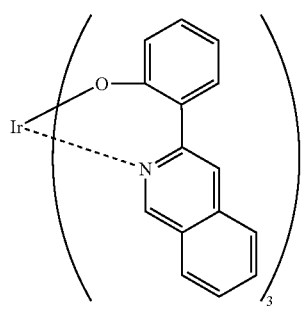
(1-69)
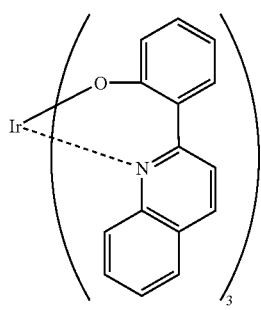

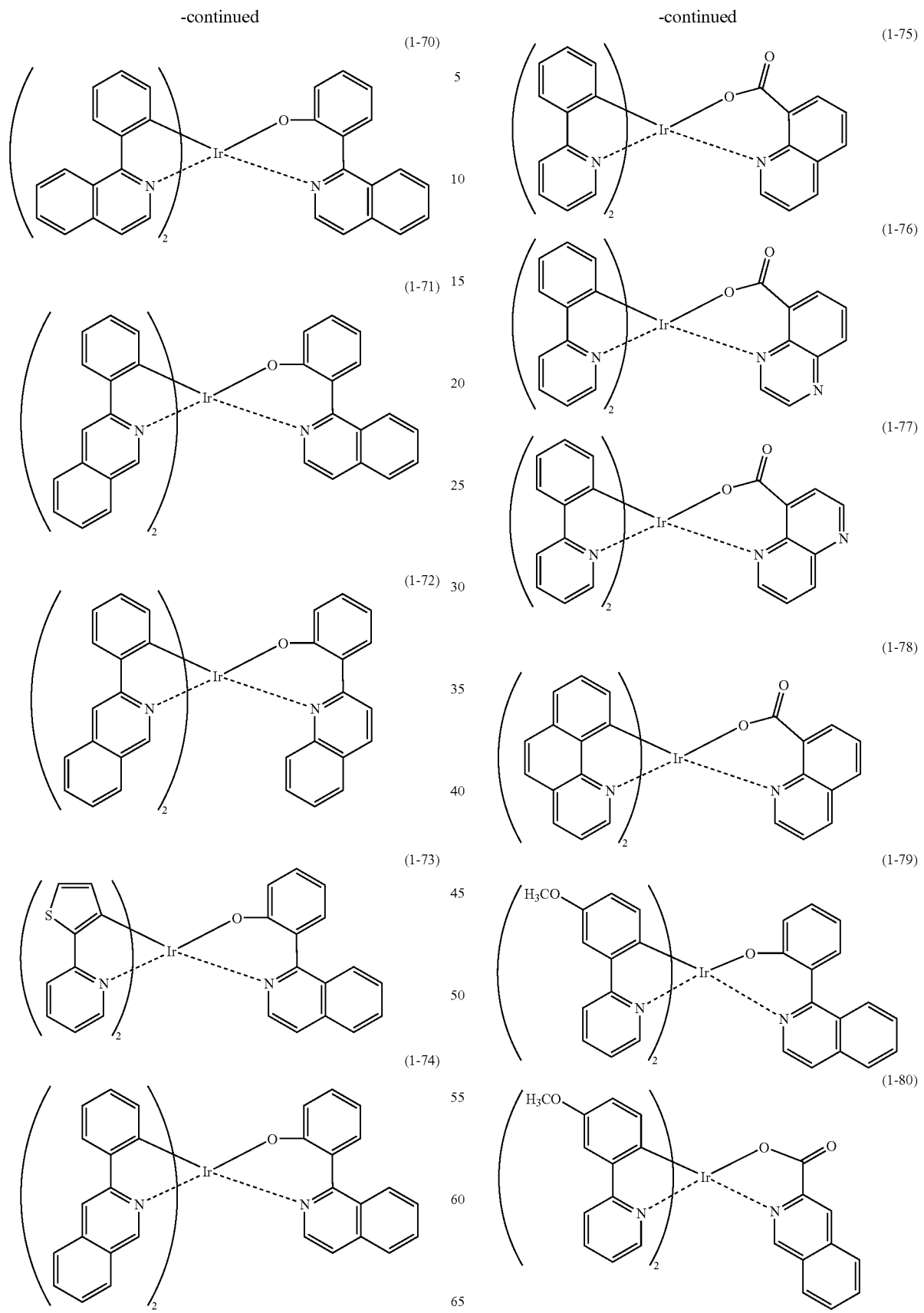

The transition metal complex of the invention can be synthesized by various measures. For example, it can be synthesized from a ligand or a dissociated body thereof and a transition metal compound in the absence or presence of a solvent (such as halogen based solvents, alcohol based solvents, ether based solvents, ester based solvents, ketone based solvents, nitrile based solvents, and water) and in the absence or presence of a base (such as various inorganic or organic bases including sodium methoxide, t-butoxypotassium, triethylamine, and potassium carbonate) at a temperature of not higher than room temperature or upon heating (in addition to the usual heating, a heating measure with microwaves is also effective).

Next, the light emitting element containing the transition metal complex of the invention will be described. The light emitting element of the invention is not particularly limited with respect to the system, driving method and utilization form so far as it is an element utilizing the transition metal complex of the invention, i.e., the transition metal complex represented by the formula (1). As representative light emitting elements, are enumerated organic EL (electroluminescent) elements.

In the light emitting element of the invention, it is preferable that the light emitting layer contains at least two kinds of host materials and at least one kind of the compound represented by the general formula (1). The host material as referred to herein means a compound mainly bearing injection and transportation of electric charges.

In the light emitting element of the invention, it is preferable that the light emitting layer contains at least two kinds of a hole transporting host material and an electron transporting host material. The hole transporting host material referred to herein means a compound mainly bearing injection and transportation of holes in the light emitting layer. The electron transporting host material as referred to herein means a compound mainly bearing injection and transportation of electrons in the light emitting layer.

The hole transporting host material is preferably an amine derivative (for examples, a triphenylamine derivative and a pyrrole derivative), and more preferably a diamine derivative (for examples, a benzidine derivative).

The electron transporting host material is preferably a nitrogen-containing hetero ring compound (more preferably, a five- or six-membered nitrogen-containing aromatic ring compound) or a metal complex (more prefereably, an aluminum complex or a zinc complex), and it is further more preferable to use complexes having a quinolinol ligand and derivatives thereof.

In the light emitting element of the invention, it is preferable to use a layer containing a compound having an ionization potential of 5.9 eV or more (more preferably 6.0 eV or more) between a cathode and a light emitting layer. It is more preferable to use a layer containing an electron transporting material (an electron transporting layer) having an ionization potential of 5.9 eV or more.

The formation method of the organic layer (organic compound layer) of the light emitting element containing the transition metal complex of the invention is not particularly limited but includes resistance heating vapor deposition, electron beam irradiation, sputtering, molecular lamination method, coating methods (such as spray coating, dip coating, impregnation, roll coating, gravure coating, reverse coating, roll brushing, air knife coating, curtain coating, spin coating, flow coating, bar coating, micro gravure coating, air doctor coating, blade coating, squeeze coating, transfer roll coating, kiss coating, cast coating, extrusion coating, wire bar coating, and screen coating), inkjet method, printing method, and transfer method. Above all, resistance heating vapor deposition, coating method, and transfer method are preferable from the standpoints of characteristics and manufacture.

The light emitting element of the invention is an element forming a light emitting layer or a plurality of organic compound films containing a light emitting layer between a pair of electrodes consisting of an anode and a cathode and may have a positive hole injection layer, a positive hole transporting layer, an electron injection layer, an electron transporting layer, a protective layer, etc. in addition to the light emitting layer. Further, these layers may be each a layer provided with other functions. For the formation of each layer, various materials can be used.

The anode is to supply positive holes into the positive hole injection layer, the positive hole transporting layer, the light emitting layer, and the like. For the anode, metals, alloys, metal oxides, electroconductive compounds, or mixtures thereof can be used, and materials having a work function of 4 eV or more are preferable. Specific examples include conductive metal oxides such as tin oxide, zinc oxide, indium oxide, and indium-tin oxide (ITO), metals such as gold, silver, chromium, and nickel, mixtures or laminates of the foregoing metals and conductive metal oxides, inorganic conductive substances such as copper iodide and copper sulfide, organic conductive materials such as polyanilines, polythiophenes, and polypyrroles, and laminates thereof with ITO; and preferably conductive metal oxides. Above all, ITO is particularly preferable from the standpoints of productivity, high conductivity, transparency, etc. The film thickness of the anode can properly be chosen but in general, is preferably in the range of from 10 nm to 5 μm, more preferably from 50 nm to 1 μm, and further preferably from 100 nm to 500 nm.

As the anode, ones having a layer formed on a soda lime glass, an alkali-free glass, a transparent resin substrate, etc. are in general used. In the case where a glass is used, for making the amount of eluted ions from the glass small, it is preferred to use an alkali-free glass with respect to its material quality. Further, in the case where a soda lime glass is used, it is preferred to use a barrier coat such as silica. The thickness of the substrate is not particularly limited so far as a sufficient mechanical strength can be kept. In the case where a glass is used, the thickness of the substrate is in general 0.2 mm or more, and preferably 0.7 mm or more.

With respect to the preparation of the anode, various methods are used depending on the material. For example, in the case of ITO, the film is formed by a method including electron beam irradiation, sputtering, resistance heating vapor deposition, chemical reaction methods (such as a sol-gel method), and coating of a dispersion of indium-tin oxide.

The anode can decrease a driving voltage of the element or enhance a light emission efficiency by washing or other processings. For the example, in the case of ITO, UV-ozone processing, plasma processing, etc. are effective.

The cathode is to supply electrons into the electron injection layer, the electron transporting layer, the light emitting layer, and the like. The cathode is selected while taking into consideration adhesion to adjacent layers thereto, such as the electron injection layer, the electron transporting layer, and the light emitting layer, ionization potential, stability, etc. As materials of the cathode, can be used metals, alloys, metal halides, metal oxides, electroconductive compounds, and mixtures thereof. Specific examples include alkali metals (such as Li, Na, and K) and fluorides or oxides thereof, alkaline earth metals (such as Mg and Ca) and fluorides or oxides thereof, gold, silver, lead, aluminum, sodium-potassium alloys or mixed metals thereof, lithium-aluminum alloys or mixed metals thereof, magnesium-silver alloys or mixed metals thereof, and rare earth metals such as indium and yttrium. Materials having a work function of not more than 4 eV are preferable, and aluminum, lithium-aluminum alloys or mixed metals thereof, and magnesium-silver alloys or mixed metal thereof are more preferable. The cathode can take not only a single layer structure of the foregoing compounds and mixtures but also a laminated structure containing the foregoing compounds and mixtures. For example, laminated structures of aluminum/lithium fluoride or aluminum/lithium oxide are preferable. The film thickness of the cathode can properly be chosen depending on the material but in general, is preferably in the range of from 10 nm to 5 µm, more preferably from 50 nm to 1 µm, and further preferably from 100 nm to 1 µm.

For the preparation of the cathode, electron beam irradiation, sputtering, resistance heating vapor deposition, coating method, and transfer can be employed. A metal alone can be vapor deposited, and two or more components can be vapor deposited at the same time. In addition, it is possible to form an alloy electrode by vapor deposition of a plurality of metals at the same time. Also, previously prepared alloys may be subjected to vapor deposition.

It is preferred that the sheet resistance of the anode and cathode is low. The sheet resistance is preferably not more than several hundred $\Omega/\square$ ($\Omega$/square).

As the light emitting layer, can be employed any materials capable of forming a layer having a function to enable to inject positive holes from the anode or the positive hole injection layer or positive hole transporting layer and to inject electrons from the cathode or the electron injection layer or electron transporting layer during the application of an electric field, a function to move injected charges, or a function to provide a field of recombination of positive holes and electrons to cause light emission. Other examples than the transition metal complex of the invention include benzoxazole, benzimidazole, benzothiazole, styrylbenzene, polyphenyl, diphenylbutaiene, tetraphenylbutadiene, naphthalimide, coumarin, perylene, perinone, oxadiazole, aldazine, piperidine, cyclopentadiene, bisstyrylanthracene, quinacridone, pyrrolopyridine, thiadiazolopyridine, styrylamine, aromatic dimethylidine compounds, various metal complexes represented by metal complexes or rare earth complexes of 8-quinolinol, polymer compounds such as polythiophenes, polyphenylenes, and polyphenylene vinylenes, organosilanes, iridium-triphenylpyridine complexes, transition metal complexes represented by platinum porphyrin complexes, and derivatives thereof. The film thickness of the light emitting layer is not particularly limited but in general, is preferably in the range of from 1 nm to 5 µm, more preferably from 5 nm to 1 µm, and further preferably from 10 nm to 500 nm.

The formation method of the light emitting layer is not particularly limited, but examples include resistance heating vapor deposition, electron beam irradiation, sputtering, molecular lamination method, coating method, inkjet method, printing method, LB method, and transfer method. Above all, resistance heating vapor deposition and coating method are preferable.

The light emitting layer may be made of a single compound or a plurality of compounds. Further, the light emitting layer may be a single layer or multiple layers, and the respective layers cause light emission of different colors and, for example, may emit a white light. In the case of a plurality of light emitting layers, the respective light emitting layers may be made of a single material or a plurality of compounds.

As the positive hole injection layer and positive hole transporting layer, can be employed materials having any one of a function to inject positive holes from the anode, a function to transport positive holes, or a function to block electrons injected from the cathode. Specific examples include carbazole, triazole, oxazole, oxadiazole, imidazole, polyarylalkanes, pyrazoline, pyrazolone, phenylenediamine, arylamines, amino-substituted chalcones, styrylanthracene, fluorenone, hydrazone, stilbene, silazanes, aromatic tertiary amine compounds, styrylamine compounds, aromatic dimethylidene based compounds, porphyrin based compounds, polysilane based compounds, poly(N-vinylcarbazole), aniline based copolymers, thiophene oligomers, conductive high-molecular weight oligomers such as polythiophene, organosilanes, carbon films, the compound of the invention, and derivatives thereof. The film thickness of the positive hole injection layer and positive hole transporting layer is not particularly limited but in general, is preferably in the range of from 1 nm to 5 µm, more preferably from 5 nm to 1 µm, and further preferably from 10 nm to 500 nm. The positive hole injection layer and positive hole transporting layer may be of a single layer structure composed of one or two or more of the foregoing materials and may also be of a multilayered structure composed of plural layers of the same composition or different compositions.

Examples of the formation method of the positive hole injection layer and positive hole transporting layer include vacuum vapor deposition method, LB method, a method of coating a solution or dispersion of the foregoing positive hole injection and transporting material in a solvent, inkjet method, printing method, and transfer method. In the case of the coating method, the positive hole injection and transporting material can be dissolved or dispersed together with a resin component. Examples of resin components include polyvinyl chloride, polycarbonates, polystyrenes, polymethyl methacrylate, polybutyl methacrylate, polyesters, polysulfones, polyphenylene oxide, polybutadiene, poly-(N-vinylcarbazole), hydrocarbon resins, ketone resins, phenoxy resins, polyamides, ethyl cellulose, polyvinyl acetate, ABS resins, polyurethanes, melamine resins, unsaturated polyester resins, alkyd resins, epoxy resins, and silicone resins.

As the electron injection layer and electron transporting layer, can be employed materials having any one of a function to inject electrons from the cathode, a function to transport electrons, or a function to block positive holes injected from the anode. Specific examples include triazole, oxazole, oxadiazole, imidazole, fluorenone, anthraquinodimethane, anthrone, diphenylquinone, thiopyran dioxide, carbodiimide, fluorenylidenemethane, distyrylpyrazine, naphthalene, aromatic ring tetracarboxylic anhydrides such as perylene, phthalocyanine, various metal complexes represented by a metal complex of 8-quinolinol and metal complexes comprising metal phthalocyanine, benzoxazole, or benzothiazole as a ligand, organosilanes, and derivatives thereof. The film thickness of the electron injection layer and electron transporting layer is not particularly limited but in general, is preferably in the range of from 1 nm to 5 µm, more preferably from 5 nm to 1 µm, and further preferably from 10 nm to 500 nm. The electron injection layer and electron transporting layer may be of a single layer structure composed of one or two or more of the foregoing materials and may also be of a multilayered structure composed of plural layers of the same composition or different compositions.

Examples of the formation method of the electron injection layer and electron transporting layer include vacuum vapor deposition method, LB method, a method of coating a solution or dispersion of the foregoing electron injection and transporting material in a solvent, inkjet method, printing method, and transfer method. In the case of the coating method, the electron injection and transporting material can be dissolved or dispersed together with a resin component. As the resin component, can be employed those enumerated above in the case of the positive hole injection layer and positive hole transporting layer.

As the protective layer, can be employed any materials having a function to suppress entrance of substances of promoting deterioration of the element, such as moisture and oxygen, into the element. Specific examples include metals such as In, Sn, Pb, Au, Cu, Ag, Al, Ti, and Ni, metal oxides such as MgO, SiO, $SiO_2$, $Al_2O_3$, GeO, NiO, CaO, BaO, $Fe_2O_3$, $Y_2O_3$, and $TiO_2$, metal fluorides such as $MgF_2$, LiF, $AlF_3$, and $CaF_2$, nitrides such as $SiN_x$ and $SiO_xN_y$, polyethylene, polypropylene, polymethyl methacrylate, polyimides, polyureas, polytetrafluoroethylene, polychlorotrifluoroethylene, polydichlorodifluoroethylene, a copolymer of chlorotrifluoroethylene and dichlorodifluoroethylene, copolymers obtained by copolymerizing a monomer mixture containing tetrafluoroethylene and at least one comonomer, fluorine-containing copolymers having a cyclic structure in the copolymer main chain, water-absorbing substances having a percentage of water absorption of 1% or more, and moistureproof substances having a percentage of water absorption of not higher than 0.1%.

The formation method of the protective layer is not particularly limited, but examples include vacuum vapor deposition method, sputtering method, reactive sputtering method, MBE (molecular beam epitaxy) method, cluster ion beam method, ion plating method, plasma polymerization method (high-frequency excitation ion plating method), plasma CVD method, laser CVD method, hot CDV method, gas source CVD method, coating method, printing method, and transfer method.

EXAMPLES

The invention will be specifically described below with reference to the following Examples, but it should not be construed that the invention is limited thereto.

(Synthesis of Illustrative Compound (1-3))

0.11 g of the following Compound a and 0.3 g of the following Compound b were dissolved in 30 mL of chloroform, to which was then added 0.03 mL of a methanol solution (28% by weight) of sodium methoxide, and the mixture was stirred under reflux for 6 hours. Water was added to the reaction mixture, and after liquid separation, an organic layer was concentrated. The resulting organic layer was purified by silica gel chromatography (solvent: ethyl acetate) to obtain 0.2 g of Illustrative Compound (1-3). This compound was irradiated with a UV light to obtain brown light emission. Luminescent spectrum (solvent: dichloromethane, $1\times10^{-5}$ moles/L, measured at 20° C.): 636 nm.

Compounds (1-1) and (1-2) can be synthesized in the same manner as in the foregoing Compound (1-3) while changing the ligand. Luminescent spectrum (solvent: chloromethane) of Compound (1-1): 620 nm, luminescent spectrum (solvent: chloromethane) of Compound (1-2): 503 nm.

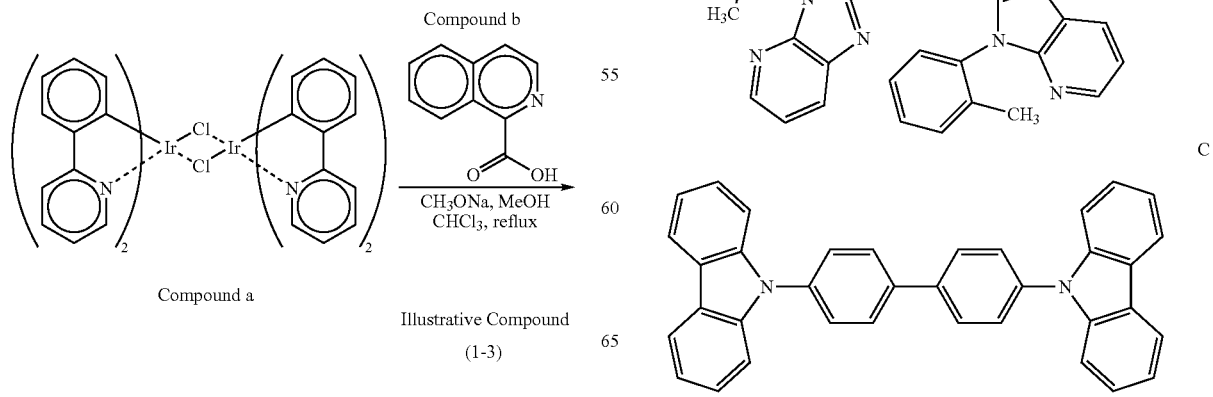

Compound a

Compound b

Illustrative Compound (1-3)

Comparative Example 1

A washed ITO substrate was placed in a vapor deposition unit and vapor deposited with TPD (N,N'-diphenyl-N,N'-di-(m-tolyl)-benzidine) in a thickness of 50 nm. The following Compound A and Compound C were then vapor deposited thereon together in a ratio of 1:17 (weight ratio) in a thickness of 36 nm, and the following Azole Compound B was further vapor deposited thereon in a thickness of 36 nm. A patterned mask (a mask having a light emitting area of 4 mm×5 mm) was placed on the organic thin film, on which were then vapor deposited successively with lithium fluoride in a thickness of 3 nm and aluminum in a thickness of 60 nm, to prepare an element. Using a source measure unit, Model 2400 manufactured by Toyo Corporation, a DC regulated voltage was applied to the EL element to cause light emission, a luminance of which was then measured using a luminance meter, BM-8 manufactured by Topcon Corporation. As a result, green light emission with a maximum luminance of 8,000 $cd/m^2$ was obtained.

Comparative Example 2

An element was prepared and evaluated in the same manner as in Comparative Example 1, except for using the following Compound E in place of the Compound A. Only feeble light emission was obtained from the element.

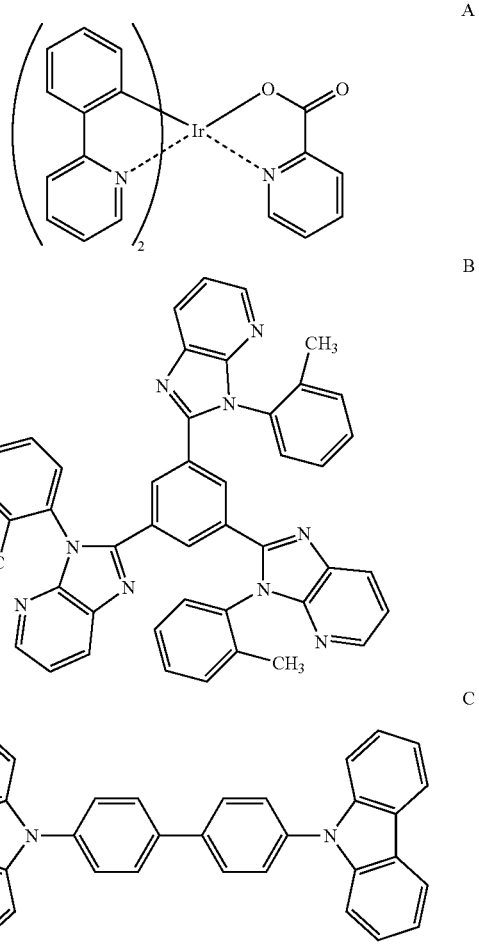

-continued

D
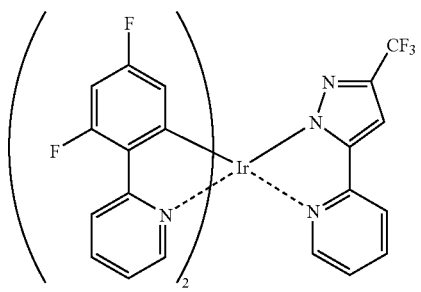

E
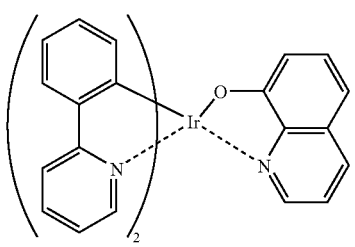

F
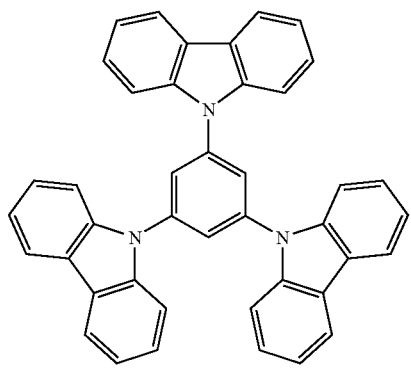

G
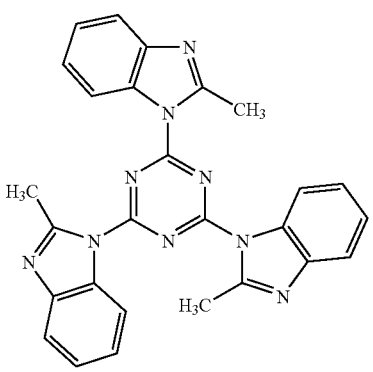

H
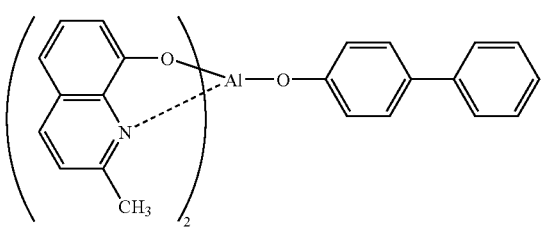

Example 1

An element was prepared and evaluated in the same manner as in Comparative Example 1, except for using Illustrative Compound (1-3) of the invention in place of the Compound A. As a result, brown light emission with a maximum luminance of 17,000 cd/m² was obtained. A lowest drive voltage (a lowest voltage at which light emission can be visually confirmed) of the element was lowered by 1 V as compared with that of the element of Comparative Example 1.

Example 2

A washed ITO substrate was placed in a vapor deposition unit and vapor deposited with TPD (N,N'-diphenyl-N,N'-di-(m-tolyl)-benzidine) in a thickness of 50 nm. The Illustrative Compound (1-3) of the invention and the foregoing Compound C were then vapor deposited thereon together in a ratio of 1:17 (weight ratio) in a thickness of 12 nm. The foregoing Compound D and Compound F were vapor deposited thereon together in a ratio of 1:17 (weight ratio) in a thickness of 24 nm, and the foregoing Azole Compound G was further vapor deposited thereon in a thickness of 36 nm. An element was prepared by cathodic vapor deposition and evaluated in the same manner as in Comparative Example 1. As a result, white light emission with a maximum luminance of 13,000 cd/m² was obtained.

Example 3

40 mg of polyvinylcarbazole and 12 mg of 2-(4-t-butylphenyl)-5-(p-biphenyl)-1,3,4-oxazdiazole were dissolved in 2.5 mL of dichloroethane, and the solution was spin coated on a washed substrate (at 2,000 rpm for 20 seconds). An organic layer had a film thickness of about 100 nm. An element was prepared by cathodic vapor deposition and evaluated in the same manner as in Comparative Example 1. As a result, brown light emission with a maximum luminance of 8,000 cd/m² was obtained.

Example 4

An element was prepared and evaluated in the same manner as in Comparative Example 1, except for using Illustrative Compound (1-1) of the invention in place of the Compound A. As a result, brown light emission with a maximum luminance of 12,000 cd/m² was obtained. A lowest drive voltage (a lowest voltage at which light emission can be visually confirmed) of the element was lowered by 1 V as compared with that of the element of Comparative Example 1.

Example 5

An element was prepared and evaluated in the same manner as in Comparative Example 1, except for using Illustrative Compound (1-2) of the invention in place of the Compound A. As a result, green light emission with a maximum luminance of 27,000 cd/m² was obtained.

Example 6

An element was prepared and evaluated in the same manner as in Comparative Example 1, except for using Illustrative Compound (1-64) of the invention in place of the Compound A. As a result, brown light emission of (x, y)=(0.56, 0.43) was obtained, and light emission with a maximum luminance of 16,700 cd/m² was obtained. An external quantum efficiency was 9.6%.

Example 7

An element was prepared and evaluated in the same manner as in Comparative Example 1, except for using Illustrative Compound (1-68) of the invention in place of the Compound A. As a result, high-luminance light emission exceeding 1,000 cd/m² was obtained.

Example 8

An element was prepared and evaluated in the same manner as in Comparative Example 1, except for using Illustrative Compound (1-75) of the invention in place of the Compound A. As a result, high-luminance light emission exceeding 1,000 cd/m² was obtained.

Example 9

An element was prepared and evaluated in the same manner as in Example 1, except for using a mixture (1:1) of TPD and Compound H in place of the Compound A. As a result, driving durability at an initial luminance of 200 cd/m² was enhanced by two times as compared with the element of Example 1.

High-luminance light emitting elements capable of emitting a light to multiple colors can be prepared in the same manner even using other compounds of the invention.

The light emitting element of the invention using the compound of the invention is able to undergo light emission with a high luminance and emits a light to multiple colors (especially brown to red colors). Accordingly, the light emitting element of the invention can suitably be used in optical fields such as display elements, displays, backlights, electrophotography, illumination light sources, recording light sources, exposure light sources, read out light sources, signals, signboards, interiors, and optical communications.

Further, the compounds of the invention can be applied to medical utilizations, fluorescent brighteners, photographic materials, UV absorbing materials, laser pigments, color filter dyes, color conversion filters, and the like.

This application is based on Japanese Patent application JP 2003-298978, filed Aug. 22, 2003, the entire content of which is hereby incorporated by reference, the same as if set forth at length.

What is claimed is:

1. An organic electroluminescent element comprising:
   a pair of electrodes; and
   at least one organic layer provided between the pair of electrodes, at least one of the at least one organic layer being a light emitting layer,
   wherein the light emitting layer comprises at least one transition metal complex represented by the formula (1):

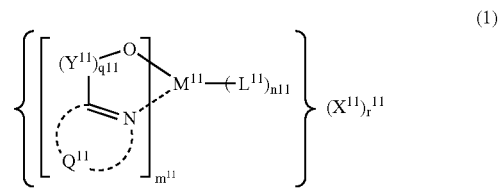

wherein $Q^{11}$ represents a group for forming a 6-membered nitrogen-containing condensed aromatic ring; $Y^{11}$ represents a connecting group; $M^{11}$ represents a transition metal ion which is one of Ru and Re; $L^{11}$ represents a ligand; $X^{11}$ represents a counter ion; $Y^{11}$ is not bonded to $Q^{11}$ to form an 8-hydroxyquinolinol ligand; $n^{11}$ represents an integer of from 0 to 4; $m^{11}$ represents an integer of from 1 to 4; $q^{11}$ represents an integer of from 0 to 3; and $r^{11}$ represents an integer of from 0 to 3.

2. An organic electroluminescent element comprising:
   a pair of electrodes; and
   at least one organic layer provided between the pair of electrodes, at least one of the at least one organic layer being a light emitting layer,
   wherein the light emitting layer comprises at least one transition metal complex represented by the formula (1):

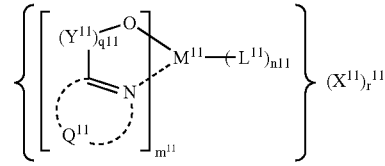

wherein $Q^{11}$ represents a group for forming a 6-membered nitrogen-containing condensed aromatic ring; $Y^{11}$ represents a connecting group; $M^{11}$ represents a transition metal ion which is one of Ir, Pt, Ru, and Re; $L^{11}$ represents a ligand; $X^{11}$ represents a counter ion; $Y^{11}$ is not bonded to $Q^{11}$ to form an 8-hydroxyquinolinol ligand; $n^{11}$ is zero; $m^{11}$ represents an integer of from 1 to 4; $q^{11}$ represents an integer of from 0 to 3; and $r^{11}$ represents an integer of from 0 to 3.

* * * * *